United States Patent
Kohli et al.

(10) Patent No.: US 8,399,704 B2
(45) Date of Patent: Mar. 19, 2013

(54) METHODS FOR SALT PRODUCTION

(75) Inventors: Rajnish Kohli, Hillsborough, NJ (US); Richard Scott Robinson, Belle Mead, NJ (US); Donghui Wu, Bridgewater, NJ (US); Wilbens Josias, North Plainfield, NJ (US)

(73) Assignee: Colgate-Palmolive Company, New York, NY (US)

( * ) Notice: Subject to any disclaimer, the term of this patent is extended or adjusted under 35 U.S.C. 154(b) by 133 days.

(21) Appl. No.: 12/866,633

(22) PCT Filed: Feb. 6, 2009

(86) PCT No.: PCT/US2009/033293
§ 371 (c)(1),
(2), (4) Date: Aug. 6, 2010

(87) PCT Pub. No.: WO2009/100267
PCT Pub. Date: Aug. 13, 2009

(65) Prior Publication Data
US 2012/0088930 A1  Apr. 12, 2012

Related U.S. Application Data

(60) Provisional application No. 61/027,433, filed on Feb. 8, 2008.

(51) Int. Cl.
*C07C 249/02* (2006.01)
(52) U.S. Cl. .................................... 562/560
(58) Field of Classification Search .................. None
See application file for complete search history.

(56) References Cited

U.S. PATENT DOCUMENTS

| | | | |
|---|---|---|---|
| 3,925,543 A | 12/1975 | Donohue | |
| 3,932,605 A | 1/1976 | Vit | |
| 3,932,608 A | 1/1976 | Anderson et al. | |
| 3,943,241 A | 3/1976 | Anderson et al. | |
| 3,988,434 A | 10/1976 | Schole et al. | |
| 4,011,309 A | 3/1977 | Lutz | |
| 4,022,880 A | 5/1977 | Vinson et al. | |
| 4,025,616 A | 5/1977 | Haefele | |
| 4,042,680 A | 8/1977 | Muhler et al. | |
| 4,064,138 A | 12/1977 | Saari et al. | |
| 4,100,269 A | 7/1978 | Pader | |
| 4,108,979 A | 8/1978 | Muhler et al. | |
| 4,108,981 A | 8/1978 | Muhler et al. | |
| 4,146,607 A | 3/1979 | Ritchey | |
| 4,154,813 A | 5/1979 | Kleinberg | |
| 4,160,821 A | 7/1979 | Sipos | |
| 4,213,961 A | 7/1980 | Curtis et al. | |
| 4,225,579 A | 9/1980 | Kleinberg | |
| 4,259,316 A | 3/1981 | Nakashima et al. | |
| 4,269,822 A | 5/1981 | Pellico et al. | |
| 4,305,928 A | 12/1981 | Harvey | |
| 4,335,102 A | 6/1982 | Nakashima et al. | |
| 4,339,432 A | 7/1982 | Ritchey et al. | |
| RE31,181 E | 3/1983 | Kleinberg et al. | |
| 4,466,954 A | 8/1984 | Ichikawa et al. | |
| 4,528,181 A | 7/1985 | Morton et al. | |
| 4,532,124 A | 7/1985 | Pearce | |
| 4,538,990 A | 9/1985 | Pashley | |
| 4,645,662 A | 2/1987 | Nakashima et al. | |
| 4,656,031 A | 4/1987 | Lane et al. | |
| 4,725,576 A | 2/1988 | Pollock et al. | |
| 4,885,155 A | 12/1989 | Parran et al. | |
| 4,919,910 A | 4/1990 | Kurtz et al. | |
| 4,997,640 A | 3/1991 | Bird et al. | |
| 5,096,700 A | 3/1992 | Siebel et al. | |
| 5,286,480 A | 2/1994 | Boggs et al. | |
| 5,334,617 A | 8/1994 | Ulrich et al. | |
| 5,370,865 A | 12/1994 | Yamagishi et al. | |
| 5,639,795 A | 6/1997 | Friedman et al. | |
| 5,747,004 A | 5/1998 | Giani et al. | |
| 5,762,911 A | 6/1998 | Kleinberg et al. | |
| 5,906,811 A | 5/1999 | Hersh | |
| 5,922,346 A | 7/1999 | Hersh | |
| 5,997,301 A | 12/1999 | Linden | |
| 6,217,851 B1 | 4/2001 | Kleinberg et al. | |
| 6,436,370 B1 | 8/2002 | Kleinberg et al. | |
| 6,488,961 B1 | 12/2002 | Robinson et al. | |
| 6,524,558 B2 | 2/2003 | Kleinberg et al. | |
| 6,558,654 B2 | 5/2003 | McLaughlin | |
| 6,805,883 B2 | 10/2004 | Chevaus et al. | |
| 6,890,497 B2 | 5/2005 | Rau et al. | |
| 2002/0081360 A1 | 6/2002 | Burgard et al. | |
| 2003/0215513 A1 | 11/2003 | Fyhr et al. | |
| 2006/0193791 A1 | 8/2006 | Boyd et al. | |
| 2007/0154863 A1 | 7/2007 | Cai et al. | |
| 2008/0233054 A1* | 9/2008 | Kleinberg et al. ............... 424/48 |
| 2009/0202456 A1 | 8/2009 | Prencipe et al. | |

FOREIGN PATENT DOCUMENTS

| | | |
|---|---|---|
| EP | 1736135 | 12/1996 |
| EP | 1135110 | 9/2001 |
| WO | WO9641617 | 12/1996 |
| WO | WO 97/032565 | 9/1997 |
| WO | WO 00/078270 | 12/2000 |
| WO | WO2007008908 | 1/2007 |
| WO | WO 09/099451 | 8/2009 |
| WO | WO 09/100267 | 8/2009 |
| WO | WO 09/100278 | 8/2009 |

OTHER PUBLICATIONS

AminoScience L-Arginine recovered from http://www.ajinomoto.co.jp/kfb/amino/e_aminoscience/bc/amino_02.html 30 on Mar. 30, 2012.*
Machado et al. CaviStat Confection Inhibition of Caries in Posterior Teeth, Abstract, 83rd Session of the American Association for Dental Research, Mar. 21-24, 2007, New Orleans, LA.
Chatterjee et al,. Bacterial Acidification and CaviStat Alkalinization of Occlusal Fissure pH, Abstract, 83rd Session of the American Association for Dental Research, Mar. 9-12, 2005, Baltimore, MD.
Kleinberg I., A Mixed-Bacteria Ecological Approach to Understanding the Role of the Oral Bacteria in Dental Caries Causation: An Alternative to *Streptococcus* Mutans and the Specific-Plaque Hypothesis, CRIT. Rev. Oral Biol. Med,. 12(2): 108-125 (2002).
Kleinberg I., A New Salvia-Based Anticaries Composition, Dentistry Today, vol. 18, No. 2, Feb. 1999.

(Continued)

*Primary Examiner* — Paul A Zucker
(74) *Attorney, Agent, or Firm* — Nikhil A. Heble

(57) ABSTRACT

The present invention provides methods to produce arginine bicarbonate more rapidly and efficiently than conventional methods.

19 Claims, No Drawings

OTHER PUBLICATIONS

Acevedo et al., "The Inhibitory effect of an arginine bicarbonate/calcium carbonate (CaviStat)—containing dentifrice on the development of dental caries in Venezuelean school children", The Journal of clinical Dentistry, 2005, v. 16, No. 3, pp. 63-70, ISSN 0895-8831.
International Search Report and Written Opinion in International Application No. PCT/US09/033293, mailed Jun. 24, 2009.
International Search Report and Written Opinion in International Application No. PCT/US10/059992, mailed May 18, 2011.
International Search Report and Written Opinion in International Application No. PCT/US10/060266, mailed Mar. 14, 2011.
Packaging with ingredient list for DenClude® (launched Dec. 2004).
Packaging with ingredient list for ProClude® (launched Jul. 2002).
Written Opinion in International Application No. PCT/US10/059992, mailed Nov. 16, 2011.
US 5,989,525, 11/1999, Kleinberg et al. (withdrawn)

* cited by examiner

METHODS FOR SALT PRODUCTION

This application claims the benefit of U.S. Ser. No. 61/027,433 filed Feb. 8, 2008, the contents of which are incorporated herein by reference.

FIELD OF THE INVENTION

The invention relates to novel methods for production of arginine bicarbonate.

BACKGROUND

Arginine bicarbonate has use in various industrial applications, including use in personal care compositions, e.g., oral care compositions. See e.g., U.S. Pat. No. 6,524,558. As the industrial requirements for arginine bicarbonate increases, so will the need for improved processes and methods to manufacture the same.

Arginine bicarbonate may be produced by bubbling carbon dioxide gas through a saturated arginine aqueous solution. However, the efficiency of the existing process needs to be improved. The existing process is slow, requiring 24 to 48 hours to complete the reaction. Carbon dioxide has very limited solubility in water, and releasing the gas into the solution produces a maximum concentration of about $1.2 \times 10^{-5}$ M at room temperature and its natural partial pressure ($3.5 \times 10^{-4}$ atmosphere). The solubility of arginine in water is only about 15% weight/weight at room temperature. Producing a concentrated arginine bicarbonate solution (e.g., about 40%) requires the continual addition of arginine to the solution, thereby increasing production time and requires constant monitoring of the reaction. Thus there is a need to improve methods to manufacture arginine bicarbonate.

SUMMARY OF THE INVENTION

The present invention is directed to an improved method for manufacturing arginine bicarbonate. The method represents a significant improvement over existing techniques, as a concentrated solution of arginine and bicarbonate anions may be produced in as little as about 10 minutes (vs. about 24-48 hours using the prior art methods), followed by faster and easier recovery processes of arginine bicarbonate salt from the solution since arginine bicarbonate solution at significantly higher concentration. e.g., 60% w/w can be produced.

The present invention includes Method 1.0, a method for producing arginine bicarbonate comprising (i) reacting an arginine slurry with carbon dioxide under controlled temperature and pressure to form a solution comprising arginine and bicarbonate anion, and (ii) optionally recovering arginine bicarbonate from the solution.

Additional methods of the present invention include Methods:

1.1 Method 1.0 wherein the arginine slurry comprises arginine and a solvent;
1.2 Method 1.1 wherein the arginine slurry comprises from about 10% to about 90% wt. arginine, e.g., about 50% wt in a solvent.
1.3 Method 1.1-1.2 wherein the solvent is water;
1.4 Of method 1.0-1.3 wherein the arginine of step (i) comprises arginine free base;
1.5 Of method 1.0-1.4 wherein the arginine is L-arginine;
1.6 Of method 1.0-1.5 wherein the arginine of step (i) comprises a salt;
1.7 Of any of the foregoing methods wherein the arginine of step (i) comprises arginine hydroxide;
1.8 Of any of the foregoing methods wherein the arginine of step (i) is comprises arginine hydrochloride;
1.9 Of any of the foregoing methods wherein the arginine of step (i) is a mixture comprising arginine in free base form and an arginine salt;
1.10 Of any of the preceding methods wherein the carbon dioxide is added to the slurry as a solid, e.g., dry ice;
1.11 Of methods 1.0-1.9 wherein the carbon dioxide is added to the slurry as a gas;
1.12 Of any of the preceding methods wherein the arginine slurry comprises from about 10% to about 90% arginine in free base or salt form;
1.13 Of any of the preceding methods wherein the carbon dioxide partial pressure is maintained at a level of greater than about 1 psi;
1.14 Of any of the preceding, methods wherein the carbon dioxide partial pressure is maintained at a level of greater than about 15 psi, e.g., greater than about 30 psi;
1.15 Of any of the preceding methods wherein the carbon dioxide partial pressure is about 5 psi to about 250 psi, e.g., about 50 to about 150 psi, e.g., about 60 to about 100 psi;
1.16 Of any of the preceding methods wherein the arginine slurry and carbon dioxide are maintained under pressure for a period greater than about 1 minute, e.g., about 1 minute to about 120 minutes, e.g., from about 1 minute to about 30 minutes:
1.17 Of any of the preceding methods wherein the arginine slurry is heated to about 30° C. to about 80° C.;
1.18 Of any of the preceding methods wherein the introduction of carbon dioxide causes the arginine slurry to be cooled;
1.19 Of any of the preceding methods wherein the arginine slurry is cooled to about 0° C. to about 40° C., e.g., about 0° C. to about 20° C.;
1.20 Of any of the preceding methods wherein the arginine slurry and carbon dioxide is agitated;
1.21 Of any of the preceding methods wherein the carbon dioxide forms carbonic acid when dissolved in the arginine slurry;
1.22 Of method 1.20 wherein the carbonic acid forms bicarbonate anion in solution;
1.23 Of any of the preceding methods wherein the initial arginine slurry has a pH of about 10 to about 14;
1.24 Of any of the preceding methods wherein the finished arginine bicarbonate solution has a pH of about 7 to about 10;
1.25 Of any of the preceding methods wherein the arginine bicarbonate is recovered from the solution by evaporation;
1.26 Of method 1.24 wherein the evaporation is by freeze drying;
1.27 Of method 1.24 wherein the evaporation is by spray drying;
1.28 Of any of the preceding methods wherein the arginine bicarbonate is recovered from the solution by precipitation;
1.29 Of any of the preceding methods further comprising the addition of an alcohol to the solution;
1.30 Of any of the preceding methods further comprising adding a bicarbonate salt, e.g., sodium bicarbonate, to the slurry or solution;
1.31 Of any of the preceding methods wherein calcium carbonate is added to the slurry or solution;
1.32 Of method 1.27 wherein the arginine bicarbonate is co-precipitated with the calcium carbonate.

1.33 Any of the foregoing methods wherein the arginine bicarbonate solution is used in formulation of a product, without fully recovering and purifying the arginine bicarbonate;

1.34 Any of the foregoing reactions wherein the pH of the solution is adjusted to pH about 8 to about 9;

1.35 Any of the foregoing methods wherein the temperature is initially raised to greater than about 50° C., e.g., to about 50 to about 70° C., e.g., about 55° C. (e.g., to enhance the solubility of the arginine), e.g., for about 5 to about 60 minutes, then lowered to from about 0° C. to about 40° C., e.g., about 0° C. to about 20° C. (e.g., to enhance the solubility of the carbon dioxide, drive the reaction to completion, and permit the reaction vessel to be opened without excessive release of carbon dioxide from the solution.).

1.36 Any of the foregoing methods wherein the initial pH of the solution is about 12.

1.37 Any of the foregoing methods wherein the final pH of the solution is about 8 to about 9.0.

DETAILED DESCRIPTION OF THE INVENTION

The present invention involves a surprisingly simple reaction to produce arginine bicarbonate salt by reacting carbon dioxide and an arginine slue under controlled temperature and pressure to form an arginine and bicarbonate anion solution, wherein the salt is then recovered from solution. The initial reaction is faster than existing methods, about 10 minutes vs. over 24 hours, and yields a more concentrated solution of arginine and bicarbonate anion (ca. 60% vs. ca. 40%).

The present method begins with the formation of an arginine slurry comprising arginine and a solvent, preferably water. As arginine free base is only slightly soluble at water at room temperature, the addition of arginine to water forms a slurry, wherein a majority of the arginine is insoluble. Any form of arginine may be utilized to form the slurry, e.g., arginine free base (in D or L form, usually L-form), or an arginine salt. It is understood that various arginine salts, e.g., hydrochloride, and pharmaceutically acceptable salts, may be substantially more soluble in water than arginine free base, and this may allow for the production of more concentrated arginine and bicarbonate anion solution. Thus, salts may be used or mixtures of free base and salts may be used in combination to form the slurry.

The slurry is produced by the addition of about 10% to about 90% weight of arginine to the solvent, e.g., about 20% to about 80%, about 30% to about 70%, about 40% to about 60%. The slurry may then be agitated to create a homogenous mixture. The initial pH of the slurry is generally about 12 for arginine free base, e.g., about 10 to about 13.

In one embodiment, the slurry may be heated to about 30° C. to about 80° C., e.g., to about 40° C., to about 50° C., to about 55° C., to about 60° C., to about 65° C., or to about 70° C. to increase the solubility of the arginine.

The reaction between carbon dioxide and water is well known in the art, wherein carbonic acid is initially formed, and disassociates into bicarbonate and hydrogen ions. The bicarbonate then further disassociates into carbonate and an additional hydrogen ion. In the present invention, carbon dioxide is added to the arginine slurry in a pressurized vessel to form bicarbonate anions, resulting in a protonated arginine (cation) and bicarbonate anion solution.

The solubility of carbon dioxide into the slurry may be increased by decreasing the temperature of the solution; however, this decreases the solubility of the arginine. Thus, a careful balance must be maintained between solubility of both components. Thus, in one embodiment, the pressurized vessel may be temperature controlled. The arginine slurry is preferably at a relatively high temperature, e.g. from about 30° C. to about 80° C., when the carbon dioxide is added to the arginine slurry, and thereafter the arginine slurry is permitted to cool to a relatively tow temperature, e.g. from about 0° C. to about 40° C.

One method of decreasing the temperature of the arginine slurry so as to increase the solubility of carbon dioxide into the slurry is to provide the carbon dioxide at a lower temperature than that of the slurry, for example by introducing carbon dioxide as dry ice, or a cooled gas. Preferably, carbon dioxide gas is used in the present reaction. Additionally, direct cooling of the slurry may be carried out.

The solubility of carbon dioxide into the slurry may he increased by increasing the partial pressure of the carbon dioxide in the reaction vessel. Thus, the reaction between the carbon dioxide and the arginine slurry may occur at about 5 psi to about 150 psi, e.g., about 50, to about 60, to about 70, to about 80, to about 90, to about 100, to about 110, to about 120, or to about 140 psi.

The reaction between the arginine slurry and carbon dioxide is then allowed to proceed for about 1 to about 120 minutes. The completion of the reaction may be gauged by monitoring the presence of undissolved arginine in the slurry, as arginine in the presence of bicarbonate anions are highly soluble compared to the arginine slurry. Another method to monitor the reaction is to measure its solution's pH in the reaction vessel directly, or sample the solution and measure its pH in an open container at room temperature.

Depending on the completion of the reaction, preferably, no solid arginine remains, and the arginine and bicarbonate anion solution is clear and colorless, additional carbon dioxide may be added to the reaction vessel.

Following the production of the arginine bicarbonate solution, the arginine bicarbonate salt may be recovered by any means known by those of skill in the art. In one embodiment, the solvent is evaporated, e.g., by heating, spray drying, or freeze drying. In another embodiment, the salt is precipitated from solution by the addition of alcohol.

The present methods may be utilized to produce arginine bicarbonate in single hatches, or may be used in a continuous process, such as in continuous stirred tank reactors, fluidized bed reactors, and plug flow reactors.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls. It is understood that when formulations are described, they may be described in terms of their ingredients, as is common in the art, notwithstanding that these ingredients may react with one another in the actual formulation as it is made, stored and used, and such products are intended to be covered by the formulations described.

The following examples further describe and demonstrate illustrative embodiments within the scope of the present invention. The examples are given solely for illustration and are not to be construed as limitations of this invention as many variations are possible without departing from. the spirit and scope thereof. Various modifications of the invention in addition to those shown and described herein should be apparent to those skilled in the art and are intended to fall within the appended claims.

EXAMPLE 1

A slurry of pH 12 containing 50% L-arginine by weight and 50% water by weight is prepared by mixing 85 g of L-arginine with 85 g of water at room temperature. The slurry is heated to 55° C. under gentle agitation. Approximately 50% of the L-arginine is determined to be dissolved by visual observation.

EXAMPLE 2

25 grams of dry ice particles are added to the slurry produced in EXAMPLE 1, and the mixture is transferred to a pressurized vessel. The dry ice is allowed to sublime in order to purge atmospheric air from the vessel, and then the vessel is sealed. Pressure in the vessel is allowed to increase to 80 psi, and the solution is maintained under pressure for 3 minutes. The vessel is opened, a small amount of unreacted arginine is observed at the bottom of the vessel.

EXAMPLE 3

The solution of EXAMPLE 2 is stirred with a spatula to make a suspension. 10 grams of dry ice is added to the vessel, and the vessel is sealed. The pressure is allowed to increase to, and maintained at 90 psi. The vessel is opened after 3 minutes, and a thick clear colorless solution is observed without precipitation. The solution has dropped to 12° C. producing an arginine bicarbonate solution of about 60% concentration, and a final pH of 8.79. Arginine bicarbonate salt is recovered by freeze drying.

EXAMPLE 4

The slurry produced in EXAMPLE 1 is transferred to a pressurized vessel, and aerated with carbon dioxide gas to obtain a carbon dioxide partial pressure of 15 psi for 5 minutes. The temperature of the reactants is lowered to 10° C. An arginine bicarbonate anion solution is formed, and arginine bicarbonate salt is recovered by spray drying.

The invention claimed is:

1. A method for producing arginine bicarbonate comprising reacting an arginine slurry with carbon dioxide under controlled temperature and pressure, wherein the partial pressure of the carbon dioxide is maintained during the reaction at a level of greater than 1 psi, to form a solution comprising arginine and bicarbonate anion, and recovering arginine bicarbonate from the solution;
   wherein sodium bicarbonate is provided to the slurry to provide the bicarbonate anion.

2. The method of claim 1 wherein the arginine slurry comprises arginine and a solvent wherein the slurry comprises about 10% to about 90% wt. arginine.

3. The method of claim 2 wherein the solvent is water.

4. The method of claim 1, wherein the arginine comprises a free base.

5. The method of claim 1, wherein the arginine is selected from L-arginine, D-arginine, or a mixture thereof.

6. The method of claim 1, wherein the arginine comprises an arginine salt.

7. The method of claim 1, wherein the arginine is selected from arginine hydroxide, arginine hydrochloride, or a mixture thereof.

8. The method of claim 1, wherein the carbon dioxide is provided to the reaction as a solid.

9. The method of claim 1, wherein the carbon dioxide is provided to the reaction as a gas under pressure.

10. The method of claim 1, wherein the arginine slurry comprises about 10% to about 90% arginine in free base or salt form.

11. The method of claim 1, wherein the carbon dioxide partial pressure is maintained during the reaction at greater than 15 psi.

12. The method of claim 1 wherein the pressure during the reaction is about 50 psi to about 140 psi.

13. The method of claim 1, wherein the arginine slurry and carbon dioxide are maintained under pressure for a period of about 1 minute to about 120 minutes.

14. The method of claim 1,wherein the arginine slurry is first heated to a temperature of from about 30°C. to about 80°C. for the duration of the reaction, then cooled to a temperature of from about 0°C. to about 40°C. after completion of the reaction.

15. The method of claim 1, wherein the arginine slurry is at a temperature of from about 30°C. to about 80°C. when the carbon dioxide is added to the arginine slurry, and thereafter the arginine slurry is permitted to cool to a temperature of from about 0°C. to about 40°C.

16. The method of claim 1, wherein the arginine slurry has a pH of about 10 to about 14.

17. The method of claim 1, wherein the arginine bicarbonate solution has a pH of about 7 to about 10.

18. The method of claim 1, wherein the arginine bicarbonate is recovered from the solution by evaporation.

19. The method of claim 1,
   wherein the pressure of the carbon dioxide is maintained during the reaction at a level of greater than 1 psi for about 1 to about 120 minutes.

* * * * *